US011518724B2

(12) United States Patent
Hannemann et al.

(10) Patent No.: US 11,518,724 B2
(45) Date of Patent: Dec. 6, 2022

(54) PROVIDING CARBON DIOXIDE BY MEANS OF OXYGEN-BASED COMBUSTION

(71) Applicant: Siemens Energy Global GmbH & Co. KG, Bayern (DE)

(72) Inventors: Frank Hannemann, Rottenbach (DE); Gerhard Zimmermann, Höchstadt/Aisch (DE)

(73) Assignee: Siemens Energy Global GmbH & Co. KG, Bayern (DE)

( * ) Notice: Subject to any disclaimer, the term of this patent is extended or adjusted under 35 U.S.C. 154(b) by 5 days.

(21) Appl. No.: 17/265,536

(22) PCT Filed: Jul. 30, 2019

(86) PCT No.: PCT/EP2019/070483
§ 371 (c)(1),
(2) Date: Feb. 3, 2021

(87) PCT Pub. No.: WO2020/030470
PCT Pub. Date: Feb. 13, 2020

(65) Prior Publication Data
US 2021/0292260 A1 Sep. 23, 2021

(30) Foreign Application Priority Data

Aug. 10, 2018 (DE) ...................... 10 2018 213 482.0

(51) Int. Cl.
*C07C 29/151* (2006.01)
*C01B 32/50* (2017.01)
(Continued)

(52) U.S. Cl.
CPC ......... *C07C 29/1518* (2013.01); *B01J 8/1827* (2013.01); *B01J 8/24* (2013.01);
(Continued)

(58) Field of Classification Search
CPC ............. C07C 9/04; C07C 1/12; C07C 41/01; C10G 2/50; C10G 2300/1022; C25B 15/02; C25B 1/04; C01B 32/50
See application file for complete search history.

(56) References Cited

U.S. PATENT DOCUMENTS

| 2016/0052785 A1* | 2/2016 | Maass ........................ C10J 3/18 252/373 |
| 2016/0206991 A1 | 7/2016 | Hafner |
| 2018/0086985 A1* | 3/2018 | von Olshausen .... B01D 53/047 |

FOREIGN PATENT DOCUMENTS

| DE | 102012214907 A1 | 10/2013 |
| DE | 102015226111 A1 | 6/2017 |
| EP | 2994216 B1 | 3/2016 |

OTHER PUBLICATIONS

PCT International Search Report and Written Opinion of International Searching Authority dated Oct. 29, 2019 corresponding to PCT International Application No. PCT/EP2019/070483 filed Jul. 30, 2019.

\* cited by examiner

*Primary Examiner* — Jafar F Parsa
(74) *Attorney, Agent, or Firm* — Wolter Van Dyke Davis, PLLC

(57) ABSTRACT

A method for preparing a carbonaceous product includes providing oxygen, in particular from electrolysis, and providing a fuel. The method also includes combusting the fuel with the oxygen by an oxy-fuel combustion process in order to provide energy, purifying a flue gas produced by the oxy-fuel combustion process, and separating carbon dioxide from the flue gas produced by the oxy-fuel combustion process, wherein energy provided by the oxy-fuel combustion process includes, in particular exclusively, heat which is used as process heat for purifying and/or for synthesising or (Continued)

providing the carbonaceous product. A corresponding system is designed to carry out the described method.

18 Claims, 1 Drawing Sheet

(51) Int. Cl.
    *C25B 9/05*         (2021.01)
    *B01J 8/18*         (2006.01)
    *B01J 8/24*         (2006.01)
    *C07C 41/01*       (2006.01)
    *C10G 2/00*        (2006.01)
    *C25B 1/04*        (2021.01)

(52) U.S. Cl.
    CPC .............. *C01B 32/50* (2017.08); *C07C 41/01* (2013.01); *C10G 2/50* (2013.01); *C25B 1/04* (2013.01); *C25B 9/05* (2021.01); *C10G 2300/1022* (2013.01); *C10G 2400/02* (2013.01); *C10G 2400/04* (2013.01); *C10G 2400/08* (2013.01)

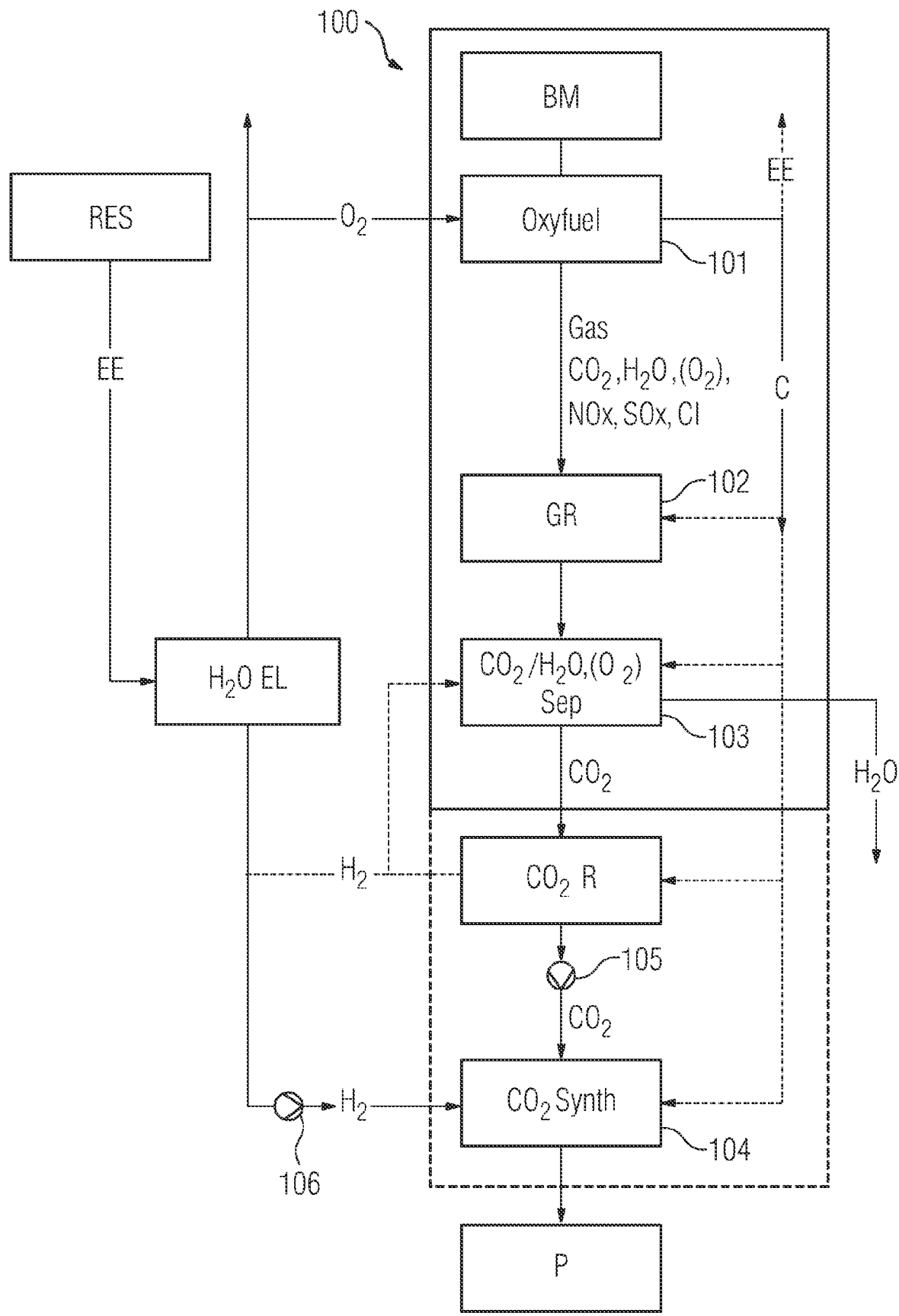

PROVIDING CARBON DIOXIDE BY MEANS OF OXYGEN-BASED COMBUSTION

CROSS REFERENCE TO RELATED APPLICATIONS

This application is the US National Stage of International Application No. PCT/EP2019/070483 filed 30 Jul. 2019, and claims the benefit thereof. The International Application claims the benefit of German Application No. DE 10 2018 213 482.0 filed 10 Aug. 2018. All of the applications are incorporated by reference herein in their entirety.

FIELD OF INVENTION

The present invention relates to a process for obtaining, providing or producing a carbon-containing or carbon-based, in particular hydrocarbon-based, product or carbon dioxide, for example for "power-to-X" (PtX) applications. Furthermore, a corresponding plant which is equipped for carrying out the process is indicated.

BACKGROUND OF INVENTION

"Power-to-gas", "power-to-liquid", "power-to-fuel" or simply "power-to-X" processes (PtX) represent promising approaches for bringing about a future conversion from fossil energy sources to an energy infrastructure which is based mainly on renewable energy sources (RES), for example wind power, solar power, geothermal energy or water power. Electricity-based or synthetic fuels are becoming ever more important, particularly in the transport sector or in industry. Such fuels, for example methane, methanol or derivatives or downstream products such as kerosene, gasoline, diesel, OME, MTBE or other hydrocarbon-based products are produced, in particular, by synthesis from hydrogen and carbon dioxide. A fundamental process can, in particular, be referred to by the name "power-to-carbon-based-fuels", "PtCbasedFuels" or "PtCbF".

Hydrogen can, in particular, be provided by electrolysis (of water). The same applies to oxygen as by- or co-product. Carbon dioxide can be taken off or separated off by various methods depending on specific applications.

Nevertheless, the provision or supply of carbon dioxide ($CO_2$), for example for PtCbF applications, is not a subject which is discussed in much detail since there are at present only relatively small projects and plans which are being realized on a small scale, for example for demonstration purposes. As a result of electricity costs which are decreasing drastically at present, for example power generation costs or power arisal costs, for renewable energy sources, in particular in places having a great potential for wind, solar power and/or photovoltaics, large-scale projects for PtCbF (for example plants having a potential of 100 MW and more) are increasingly being regarded as an advantageous solution, and thus being discussed and assessed.

Possible sources of carbon dioxide are basically flue gases or process offgases from which carbon dioxide can be obtained/recovered using, for example, "post-combustion capture" of the carbon dioxide by means of a flue gas scrub.

A process for separating carbon dioxide from a gas stream, in particular from a flue gas stream, and also a separation apparatus for carbon dioxide from such a stream is, for example, known from EP 2994216 B1.

A process for producing carbon-based secondary energy carriers or basic chemicals by coupling of an oxyfuel combustion of carbon-based fuels and a high-temperature solid electrolyte electrolysis (HT-SOEL) is adequately known from DE 10 2015 226 111 A1.

Furthermore, it is possible to recover carbon dioxide from biological processes (fermentation), "coal-to-liquid" processes, for example by means of a (process-inherent) capture preceding the actual production of the fuel or energy carrier or even by separation of carbon dioxide from air, known as DAC ("direct air capture").

In the case of power-to-gas (PtG) or power-to-liquid (PtL) applications, $CO_2$ can be transported and made available by appropriate logistics and traffic routes in places which are far-removed, in particular spatially, from conventional industries for fossil fuel-based energy generation or in regions having little potential for carbon dioxide recovery. However, this is costly since the carbon dioxide in many cases needs to be purified and liquefied in an expensive manner for this purpose.

The abovementioned solution of separating off carbon dioxide by means of DAC is, as indicated, likewise costly and still in the development phase. There are at present still only few suppliers of this technology.

SUMMARY OF INVENTION

It is therefore an object of the present invention to provide means of solving the above-described problems, in particular to provide means which allow an improved PtCbF solution.

This object is achieved by the subject matter of the independent claims. Advantageous embodiments are subject matter of the dependent claims.

One aspect of the present invention relates to a process suitable for producing, obtaining or providing carbon dioxide or a carbon-containing, in particular hydrocarbon-based, product, advantageously a secondary energy carrier, propellent, fuel, solvent or similar products, chemical raw materials or intermediates.

The process comprises the provision of oxygen, in particular from an electrolysis, and the provision of a fuel.

The process further comprises the, in particular oxygen-based, combustion of the fuel provided by means of the oxygen in an oxyfuel process or an oxygen-based process for the provision of energy, in particular heat.

In the process described, the combustion is advantageously carried out using pure or virtually pure oxygen, for example by the oxyfuel process (from "oxy" for oxygen and "fuel"), with the oxygen advantageously originating from an electrolysis which is part of the PtCbF process.

The oxygen-based combustion process, in particular oxyfuel process, is advantageously a process in which particularly high flame temperatures can be attained. It can be used both for gaseous fuels and for liquid and solid fuels. In contrast to conventional combustion using air (air-based combustion), the fuel is burnt using (virtually) pure oxygen, i.e., for example, with only a small proportion, if any, of nitrogen and noble gases.

In order to be able to influence the resulting flame temperature, a particular amount of offgas or flue gas (cooled) is usually recirculated, i.e., for example, blown together with the fuel and the oxygen into a combustion chamber. The flame temperature is, for example, dependent on the temperature of the recirculated flue gas stream. As an alternative to flue gas recirculation, the temperature in a combustion zone can also be achieved by cooling, for example by means of heating surfaces through which water and steam pass or "heat pipes".

The oxyfuel process is also particularly suitable as basis for processes which allow a removal and thus sequestration of the carbon dioxide ($CO_2$) arising or formed during combustion.

In these combustion processes, fluidized beds, in particular, can be employed for combustion of the fuel.

The abovementioned energy is advantageously made available or provided as nonfluctuating energy (electric energy and/or heat), with it being ensured that the energy is reliably, predictably and/or unconditionally available and quantifiable.

The process further comprises purification of a flue gas formed or arising as a result of the oxyfuel process. This purification can, in particular, comprise fine purification and/or dedusting of the flue gas.

The process further comprises removal, separation or recovery of carbon dioxide from the (purified) flue gas formed or arising as a result of the oxyfuel process.

Furthermore, the process can, for example, comprise a subsequent (further) $CO_2$ purification, i.e. purification of the carbon dioxide which has been separated off. The $CO_2$ purification can advantageously be carried out by reaction of remaining or residual oxygen with hydrogen.

In the process described, the energy provided by the oxyfuel process or oxygen-based processes comprises, advantageously exclusively, heat which is utilized as process heat for the purification and/or synthesis or provision of the carbon-containing product, in particular hydrocarbon-based product. In this way, heat can be used reliably and in particular without fluctuation or volatility for the further required process steps, for example the start-up or keeping hot of a synthesis apparatus, an electrolyzer or for the abovementioned purposes. In particular, turbines, gas engines or electric heating devices which would otherwise be necessary as, for example, "back-up" solution become obsolete. As a further advantage, the separated-off carbon dioxide or a product based thereon can be produced and offered for sale particularly advantageously according to this embodiment since, in particular, the efficiency of the combustion process and electric energy generation or transformation do not have to meet any demanding requirements.

In the case of methanol as product into which the carbon dioxide is to be converted or as energy carrier, this process heat can also be used, in particular, for the purification and/or distillation of crude methanol which can be present as intermediate.

If the oxygen and/or the hydrogen is provided by means of an electrolysis, fractionation of air, which is very complicated and costly, can advantageously also be dispensed with as a result of the process described.

The process described and a plant likewise presented here (see below) thus provide means for making carbon dioxide available in an improved way, in particular more efficiently and more simply, in places without sufficient sources or opportunities for procurement. In other words, carbon dioxide can be made available largely self-sufficiently in places where it is needed without a requirement for an existing industrial infrastructure comprising power station or process technology. The latter is required namely at the corresponding places of formation for, in particular, $CO_2$ imports via conventional routes or deliveries.

Furthermore, oxygen originating from an electrolysis, which is otherwise usually formed in excess and has to be blown off, can advantageously be utilized further in an advantageous way.

As described further below, oxyfuel processes taking place at atmospheric pressure or else at superatmospheric pressure, which advantageously supply precompressed $CO_2$, can be employed for the combustion.

In one embodiment, the process comprises the provision of hydrogen, in particular from an electrolysis. This electrolysis is advantageously the same electrolysis process from which the oxygen has already been provided, as described above. In this way, the abovementioned materials can be made available and utilized particularly efficiently and simply.

In one embodiment, the carbon dioxide which has been separated off is, within the process described, reacted with the hydrogen provided to synthesize a carbon-containing, in particular hydrocarbon-based, product, advantageously an energy carrier or fuel. In this embodiment, hydrogen or residual hydrogen can be present in the product separated off (carbon dioxide). In contrast to conventional combustion processes with sequestration, this does not interfere in the present process or is even advantageous when a carbon-containing product, for example methanol, is provided or produced from the carbon dioxide.

In one embodiment, the synthesis of the carbon-containing product, in particular methanol, or the reaction comprises a reverse water gas shift reaction. In this embodiment, carbon dioxide can advantageously be reacted (endothermically) with hydrogen to form carbon monoxide and water. At the same time, heat provided by the oxyfuel process can advantageously be utilized for the reaction mentioned (RWGS process).

In one embodiment, the carbon-containing product, in particular hydrocarbon-containing product, is a secondary energy carrier, for example a propellent or fuel, or an organic solvent.

Although there is at present not any accepted or standardized definition of a fuel or propellent as being "renewable" or "green", in the case of the product which can be produced and generated by means of the present invention or the above-described process, the attribute "green" can be recognized and/or certified at least for the case when $CO_2$ is produced or obtained from biomass or similar sources and, for example, hydrogen is produced or obtained from renewable energy sources.

In one embodiment, the carbon-containing product, in particular hydrocarbon-based product, is or denotes methane, methanol, MTBE (methyl tert-butyl ether) as fuel additive, DME (dimethyl ether) as organic solvent, OME (polyoxymethylene dimethyl ether) as synthetic fuel, kerosene, gasoline, diesel and/or waxes.

In one embodiment, the fuel is biomass or biomass-based, for example standardized, fuel which is, for example, traded or tradable worldwide and can be present or obtainable in pressed form or pellet form. This embodiment simplifies, in particular, the provision of the fuel. Likewise, the fuel can be provided in reproducible form, which can in turn simplify subsequent combustion since parameters of the combustion, for example a stoichiometry, can be set and laid down more simply. Combustion of the fuel from commercial, standardized biomass pellets or biomass tablets is further characterized by a comparatively low level of impurities, so that, for example, a subsequent gas purification can be simplified. In particular, the occurrence of nitrogen oxides, sulfur oxides or chlorine is in this case predictable and advantageously low, which assists filtration or purification of these substances.

The abovementioned fuel, in particular biomass, can advantageously be traded in a simple manner and, in particular, as standardized product be pretreated, transported over long distances and made available for energy generation and/or heat generation close to an installed PtCbF plant or be integrated into the latter. Furthermore, the above-described biomass-based fuel tablets are advantageously stable and barely degrade as a result of a small degree of contamination and/or water content.

In one embodiment, the fuel is a bio oil or a pyrolysis oil or pyrolytically produced oil.

In one embodiment, the provision of oxygen and/or hydrogen occurs with the aid of fluctuating, volatile or variable renewable energy, in particular via an electrolysis. Such renewable energy sources are naturally subject to fluctuations in availability, which is frequently not sufficiently predictable for a continuous demand.

In an alternative embodiment, the provision of hydrogen occurs from hydrothermal and/or geothermal sources, i.e. in particular with little or no fluctuation.

In one embodiment, the provision of the energy occurs by combustion of the fuel in a nonfluctuating, i.e. nonvolatile or nonvariable, way. In contrast to the renewable energy sources, the energy "obtained" or "produced" by the oxygen-based combustion of the fuel can be provided quantifiably, continuously and reliably.

A further aspect of the present invention relates to a plant, in particular a PtCbF plant, which is equipped for carrying out the process described here or substeps thereof. The plant comprises, in particular, a combustion apparatus, a gas purification, a $CO_2$ removal device and, in particular, a facility for converting carbon dioxide and hydrogen into the carbon-based product.

By means of the plant described below, in particular comprising a fluidized bed, energy can be quickly and cheaply made available from an appropriate (biomass-based) waste material or fuel.

In particular, the plant described can be installed and the process described can be carried out or employed at places where there is a large capacity for renewable energies, i.e. where large quantities of these energies are expected to be able to be produced. Due to the tendency of the price (for example price per kilowatt hour generated) of the renewable energies to decrease, a demand or offtake of these energies will increase or become increasingly lucrative. Associated therewith, these energy sources will increasingly also be demanded for ecologically sustainable PtX applications.

In one embodiment, the provision of hydrogen is effected by or from an electrolysis, in particular a PEM ("PEM"="polymer electrolyte membrane") electrolysis.

In one embodiment, the provision of oxygen is effected by or from an electrolysis, in particular a PEM electrolysis.

In one embodiment, both the provision of oxygen and also the provision of hydrogen is effected from or by a PEM electrolysis.

This PEM or water-based electrolysis is known from the prior art.

In one embodiment, the electrolysis is carried out under elevated pressure, for example relative to atmospheric pressure, so that the electrolysis products, in particular oxygen and hydrogen, are likewise present under elevated pressure and can be processed further under this pressure. This offers the advantage that less compression work subsequently has to be carried out.

In one embodiment, the electrolysis products, in particular oxygen and hydrogen are compressed or provided in pressurized form only after they have been electrolytically produced. Here, the actual electrolysis can be carried out under ambient or atmospheric pressure.

In the case of such a high-pressure or pressure electrolysis, the downstream combustion can likewise be carried out under elevated pressure and correspondingly more simply or efficiently, for example by carbon dioxide being provided under conditions which are ideally matched to downstream synthesis steps or substeps.

A subsequent gas purification can advantageously be simplified at the same time in embodiments in which the electrolysis products are compressed, since impurities in the fuel, for example chlorine, nitrogen, nitrogen oxides or sulfur oxides, can be dissolved or removed more easily. In particular, the nitrogen oxides and sulfur oxides are firstly formed here and only then are chlorine or chlorine compounds formed.

In one embodiment, a constant proportion of oxygen, in particular a proportion which is not directly burnt, is, in the course of the process described, reacted with the hydrogen provided to form water for the above-described carbon dioxide removal or a carbon dioxide purification. As a result of this embodiment, removal of oxygen by starting materials or products already present can also be simplified. Particularly in the case of oxygen-based combustion (oxyfuel process), a $CO_2$ gas or $CO_2$ flue gas still contains small amounts of oxygen which can subsequently be reacted with hydrogen likewise originating from, for example, an electrolysis to form water.

In one embodiment, the energy provided by the oxyfuel process or oxygen-based process comprises, in particular exclusively, heat which, in the course of the process described, is utilized for subsequent power-heat coupling. In this way, conventional power stations, for example steam power stations or combined heating-power stations, can advantageously continue to be used.

In one embodiment, the energy provided by the oxyfuel process or oxygen-based process comprises electric energy which is obtained as nonfluctuating or nonvolatile energy or energy source, for example via a steam power process. In this embodiment, the oxygen and/or the fuel can advantageously be utilized for power generation which utilizes, for example, electric power as by-product for feeding into a power grid or as grid compensation ("peaker") for or in addition to a plant which is possibly provided and provides the oxygen in the hydrogen from, for example, renewable or regenerative energy sources.

In one embodiment, the oxyfuel process or oxygen-based combustion process is carried out without flue gas recirculation (see above). In this embodiment, the combustion can be carried out particularly efficiently.

In one embodiment, an appropriately constructed fluidized bed is used for combustion of the fuel which is, in particular, biomass or biomass-based.

Embodiments, features and/or advantages which relate in the present text to the process described can also apply to the plant, or vice versa.

Further features, properties and advantages of the present invention will be described in more detail below with the aid of working examples with reference to the accompanying FIGURE. All features described above and in the following are advantageous both individually and in combination with one another. It goes without saying that other embodiments can be utilized and structural or logical changes can be carried out without going outside the scope of protection of the present invention. The following description is therefore not to be interpreted as constituting a restriction.

Functional details disclosed here are therefore not to be construed as restrictions, but instead only as illustrative basis which offers a person skilled in this field of technology guidance for using the present invention in a variety of ways.

The expression "or" or "and/or" used here if used in a series of two or more elements means that each of the elements listed can be used alone or it is possible to use any combination of two or more of the elements listed.

Further details of the invention will be described below.

BRIEF DESCRIPTION OF THE DRAWINGS

FIG. 1 schematically shows, in simplified form, a process sequence of the process of the invention in the form of a flow or block diagram.

DETAILED DESCRIPTION OF INVENTION

In the working examples and in the FIGURE, identical elements or elements having the same effect can in each case be denoted by identical reference symbols. The elements depicted and their relative sizes are basically not to be regarded as being true to scale, but instead individual elements can be depicted exaggeratedly thick or large for better presentation and/or for better understanding.

FIG. 1 indicates, in simplified form, a process according to the invention for producing or providing carbon dioxide or a carbon-containing product, in particular hydrocarbon-based product, P.

FIG. 1 shows, inter alia, a plant 100. The plant 100 is advantageously equipped for providing a carbon-containing product, for example also pure carbon, or in particular a hydrocarbon-based product. In particular, the plant 100 is advantageously a PtCbF plant ("power-to-carbon-based fuels"), i.e. equipped for providing the abovementioned product, in particular a fuel, from energy provided, for example from renewable sources and/or the oxygen-based combustion of a fuel.

For this purpose, the plant 100 advantageously comprises a combustion apparatus 101. The combustion apparatus 101 is advantageously equipped for oxygen-based combustion of a fuel, advantageously a biomass-based fuel, in particular biomass BM. Accordingly, the combustion apparatus is advantageously an oxyfuel combustion plant.

The combustion apparatus 101 is accordingly advantageously made for the combustion of biomass. As an alternative, the combustion apparatus can also be equipped and designed for combustion of biological fuels or energy carriers, for example bio oils or pyrolytically produced oils.

However, advantage is given to using biomass BM, in particular in pressed and standardized form, for the fuel since this product is, in particular, more readily marketable or producible and more suitable for long-range transport.

In addition, this form of fuel gives more reproducible combustion results and/or products. The abovementioned biomass can, for example, be provided by processes known in the prior art in the form of tablets or pellets which can be provided by means of drying measures, in particular torrefication, tableting and/or pressing ("pelleting"). A particularly high-quality tablet is formed by additional torrefication of the biomass, which can encompass a drying measure at temperatures above 250° C. Corresponding tablets or pellets are typically obtained from wood, wood offcuts or comparable raw materials. Furthermore, these fuels or energy carriers can be burnt or concomitantly burnt in conventional air-based steam power stations.

Depending on the precise shape and composition of the, in particular biomass-based, fuel to be burnt in the oxygen-based combustion, a flue gas formed (in FIG. 1 denoted as "gas") can, for example, contain waste products such as nitrogen oxides ($NO_x$), sulfur oxides ($SO_x$) and/or chlorine (Cl), chlorine compounds or further substances in addition to $CO_2$ and water.

In the course of the process described, oxygen ($O_2$) which advantageously originates from an electrolysis, advantageously a PEM electrolysis (see below), to be fed, in particular, as oxidant to a combustion should be burnt in a minimally superstoichiometric amount in the combustion apparatus 101, i.e. so that a small proportion of oxygen can still be present in the flue gas. This is most advantageous and most efficient in view of the difficulty or impossibility of carrying out precisely stoichiometric combustion. Furthermore, this can be necessary or advantageous in order to avoid formation of dioxins and (other) toxic hydrocarbons. This residual oxygen in the $CO_2$ normally has to be removed by means of complicated purification measures comprising, for example, activated carbon filters or molecular sieves.

The above-described combustion apparatus 101 comprises, for example, a fluidized bed or other means, for example gratings, for holding the fuel in place in the gasification of a fuel possibly provided in solid form ("biomass pellet"). The use of a fluidized bed for the gasification and/or combustion of the fuel is advantageous since it in principle allows a possibly more inefficient flue gas recirculation in the course of the oxyfuel process to be dispensed with or the recirculation to be reduced.

However, the combustion can in principle be carried out with and without $CO_2$ recirculation.

The plant 100 advantageously further comprises a gas purification 102. The gas purification or gas purification facility 102 can, for example, be equipped so as to purify, and in particular also remove dust from, the flue gas formed by combustion (cf. reference symbol "GR" for the process step of gas purification in FIG. 1).

The plant 100 advantageously further comprises a $CO_2$ removal device 103. The removal device 103 can, in particular, be equipped for separating waste products which can inherently be present in the fuel, from the carbon dioxide obtained or to be obtained, in particular by condensing out water. The waste materials mentioned can, for example, comprise nitrogen oxides ($NO_x$), sulfur oxides ($SO_x$) and/or chlorine or further substances.

A pump or transport device 105 by means of which the carbon dioxide can be fed to a downstream synthesis can also be seen in FIG. 1.

Furthermore, the plant 100 comprises an apparatus 104 for converting carbon dioxide and hydrogen into the carbon-containing product described.

It can also be seen in FIG. 1 that, for example, a further $CO_2$ purification ($CO_2$—R) can be carried out subsequent to the gas purification and/or the removal of the $CO_2$ in order to provide carbon dioxide in high-purity form for the synthesis of the product P.

For the carbon dioxide removal or separation (cf. reference symbol "Sep" for the process step of removal/separation in FIG. 1) or a carbon dioxide purification GR, it is possible, in particular, to react a residual proportion of oxygen $O_2$, i.e. for example oxygen originating from the superstoichiometric oxyfuel combustion and/or the electrolysis, with provided hydrogen $H_2$ to form water $H_2O$ (this is indicated by the broken-line arrow and the reference symbol $H_2$).

The apparatus 104 is, in particular, designed or equipped for the synthesis (cf. reference symbol "Synth" for the process step of the reaction or synthesis in FIG. 1) of the carbon-containing, in particular hydrocarbon-based, product. For example, the apparatus 104 can be designed for reacting, with introduction of hydrogen, in particular from a (or produced by a) PEM electrolysis, the carbon dioxide which has been separated off into the carbon-containing product P. The carbon-containing product P can be methane, methanol, MTBE, DME, OME, kerosene, gasoline, diesel, comparable fuels or additives, products produced or able to be produced by the Fischer-Tropsch synthesis or waxes. The products mentioned are of particular importance industrially or in particular for mobility purposes.

In the conventional methanol synthesis in particular, synthesis gas (for example a mixture of $H_2$, CO and $CO_2$) is, for example, used as starting material and reacted under high pressures and at high temperatures. For example, the reaction of hydrogen and the carbon dioxide obtained by the process described can be carried out by means of the Sabatier process.

The reaction or synthesis of the further abovementioned products can be carried out analogously by known methods.

For the provision of the starting materials for the process described, in particular oxygen $O_2$ and hydrogen $H_2$, reference is made to the left-hand side of FIG. 1. In the process described, renewable energy sources RES are advantageously employed as energy source or for operating an electrolysis, advantageously a water-based PEM electrolysis. The electrolysis process is denoted by the reference symbol EL in FIG. 1. Electrolysis products formed are, as is known, oxygen $O_2$ (see upper part of FIG. 1) and hydrogen $H_2$ (cf. lower part of FIG. 1).

The products oxygen and hydrogen can, for example, be temporarily stored in the case of an undersupply of renewable energy sources, even in advance, by known means, so that the above-described combustion (oxyfuel process) can be carried out predictably and continuously.

The vertical upward-pointing arrow in the upper part of the FIGURE (oxygen path) indicates that oxygen is possibly produced in excess and has to be blown off, or can advantageously be utilized in another way.

In order to convey these substances, in particular make the oxygen available for the combustion, and the hydrogen to the apparatus 104, it is possible to employ a compressor (cf. reference symbol 106 in FIG. 1) or another transport or compression device.

The abovementioned electrolysis, which is, for example, supplied with electric energy EE from the renewable energy sources RES, can optionally be carried out under elevated pressure so that the electrolysis products, oxygen $O_2$ and hydrogen $H_2$, are likewise present under elevated pressure. As an alternative or in addition, oxygen $O_2$ and hydrogen $H_2$ can be compressed after they have been electrolytically produced. The pressures or gauge pressures mentioned can assume values in the range from 20 to 80 bar or more.

A significant aspect of the process described relates to the embodiment in which the energy E provided by the oxyfuel process comprises, in particular exclusively, heat C which can be made available for further purposes, for example be utilized as process heat for the removal of carbon dioxide $CO_2$, for the purification and/or for a synthesis or provision of the carbon-containing product P.

A $CO_2$-based synthesis, e.g. of methanol, could comprise, for example, a reverse CO conversion or reverse water gas shift reaction (RWGS) in a first step. Here, $CO_2$ is endothermically reacted with $H_2$ to form CO and $H_2O$. The actual synthesis could then take place furthermore by conventional means using the resulting mixture of CO and $H_2$ (corresponds, for example, to a classical synthesis gas). The abovementioned heat from the oxygen-based combustion can advantageously be utilized for the RWGS process described.

The abovementioned heat can likewise be utilized for subsequent power-heat coupling.

As an alternative or in addition to the abovementioned embodiments, the energy E provided by the oxyfuel process can comprise electric energy EE which is obtained as nonfluctuating energy, for example by means of a steam power process.

The invention is not restricted to the working examples by the description of these, but encompasses each new feature and each combination of features. This includes, in particular, any combination of features in the claims, even when this feature or this combination itself is not explicitly indicated in the claims or working examples.

The invention claimed is:

1. A process for producing a carbon-containing product, comprising:
   providing oxygen (O2), and a fuel,
   combusting the fuel by means of the oxygen (O2) in an oxyfuel process to provide energy,
   purifying a flue gas formed by the oxyfuel process, and
   separating carbon dioxide (CO2) from the flue gas formed by the oxyfuel process, comprising reacting the oxygen (O2) in the flue gas with hydrogen (H2) to form water (H2O),
   wherein the energy provided by the oxyfuel process comprises heat which is utilized as process heat for a CO2-based synthesis that produces the carbon-containing product and that comprises an endothermic reaction.

2. The process as claimed in claim 1,
   wherein hydrogen (H2) is provided and the carbon dioxide (CO2) which has been separated off is reacted with the hydrogen (H2) in the CO2-based synthesis to give the carbon-containing product.

3. The process as claimed in claim 2,
   wherein the CO2-based synthesis comprises a reverse water gas shift reaction.

4. The process as claimed in claim 1,
   wherein the carbon-containing product is a secondary energy carrier.

5. The process as claimed in claim 1,
   wherein the carbon-containing product is methane, methanol, MTBE, DME, OME, kerosene, gasoline, diesel and/or waxes.

6. The process as claimed in claim 1,
   wherein the fuel is biomass or biomass-based, and/or a standardized fuel present in pressed form or pellet form.

7. The process as claimed in claim 1,
   wherein the provision of the oxygen (O2) and/or hydrogen (H2) occurs by means of fluctuating renewable energy and the provision of the energy occurs in a nonfluctuating manner.

8. The process as claimed in claim 2,
   wherein the provision of the oxygen (O2) and/or the provision of the hydrogen (H2) occurs by means of an electrolysis.

9. The process as claimed in claim 8,
   wherein the electrolysis is carried out under elevated pressure so that the oxygen (O2) and the hydrogen (H2) are likewise present under elevated pressure or the oxygen (O2) and the hydrogen (H2) are provided in compressed form after they have been produced electrolytically.

10. The process as claimed in claim 1, further comprising a further carbon dioxide purification step subsequent to separating the carbon dioxide (CO2) from the flue gas and comprising reacting the oxygen (O2) in the flue gas with hydrogen (H2) to form water (H2O).

11. The process as claimed in claim 1, wherein the energy provided by the oxyfuel process comprises heat which is utilized for subsequent power-heat coupling.

12. The process as claimed in claim 1, wherein the energy provided by the oxyfuel process comprises electric energy which is obtained as non-fluctuating energy.

13. The process as claimed in claim 1, wherein the oxyfuel process is carried out without flue gas recirculation.

14. The process as claimed in claim 1, wherein a fluidized bed is used for the combustion of the fuel.

15. The process as claimed in claim 1, wherein the energy provided by the oxyfuel process comprises exclusively heat.

16. The process as claimed in claim 3, wherein the carbon-containing product comprises methanol.

17. The process as claimed in claim 12, wherein the energy provided by the oxyfuel process comprises electric energy which is obtained as non-fluctuating energy, by means of a steam power process.

18. The process as claimed in claim 1, wherein the fuel is combusted in a minimally superstoichiometric amount that is effective to ensure some of the oxygen (O2) remains unburnt and part of the flue gas.

\* \* \* \* \*